United States Patent [19]

Lugos

[11] Patent Number: 4,917,500
[45] Date of Patent: Apr. 17, 1990

[54] COLOR SENSOR SYSTEM FOR THE RECOGNITION OF OBJECTS WITH COLORED SURFACES

[75] Inventor: Attila Lugos, Haguenau, France

[73] Assignee: Siemens Aktiengesellschaft, Berlin and Munich, Fed. Rep. of Germany

[21] Appl. No.: 278,092

[22] Filed: Nov. 30, 1988

[30] Foreign Application Priority Data

Dec. 3, 1987 [DE] Fed. Rep. of Germany ....... 3740998

[51] Int. Cl.$^4$ .............................................. G01J 3/50
[52] U.S. Cl. .................................... 356/406; 356/425; 250/226
[58] Field of Search ............... 356/402, 406, 407, 405, 356/425; 250/226

[56] References Cited

U.S. PATENT DOCUMENTS

| | | | |
|---|---|---|---|
| 3,336,481 | 8/1967 | Nelson | 250/226 |
| 4,678,338 | 7/1987 | Kitta et al. | 356/402 |
| 4,838,697 | 6/1989 | Kurandt | 356/406 |

FOREIGN PATENT DOCUMENTS

| | | | |
|---|---|---|---|
| 0049905 | 4/1982 | European Pat. Off. | |
| 0109686 | 5/1984 | European Pat. Off. | |
| 0256970 | 2/1988 | European Pat. Off. | |
| 0016826 | 2/1981 | Japan | 356/402 |
| 0060324 | 4/1984 | Japan | 356/402 |
| 0060326 | 4/1984 | Japan | 356/402 |
| 0060327 | 4/1984 | Japan | 356/402 |
| 0231427 | 12/1984 | Japan | 356/402 |
| 1410823 | 10/1975 | United Kingdom | 356/402 |

OTHER PUBLICATIONS

Patent Abstracts of Japan, vol. 8, No. 163, Jul. 27, 1984, JP-A-59 60 324.
Patent Abstracts of Japan, vol. 6, No. 171, Sep. 4, 1982, JP-A-57 90 145.
Elektrotechnik, vol. 69, No. 3, Feb. 27, 1987, pp. 28–32, 37–38.

*Primary Examiner*—F. L. Evans
*Attorney, Agent, or Firm*—John Francis Moran

[57] ABSTRACT

The color sensor system has at least three electronic light transmitters each emitting light of a determined narrow-band range of wavelengths, which under the control of a transmission control device in the course of a control cycle, illuminate successively the colored surface of the object in question for a brief period of time with light pulses of a predetermined intensity. The light reflected in each case from the colored surface upon the arrival of the light pulses is received by an electronic light receiver and converted into electrical signals. The electrical signals that are emitted successively by the light receiver in the course of a control cycle are conducted to an evaluation device for a color determination.

13 Claims, 4 Drawing Sheets

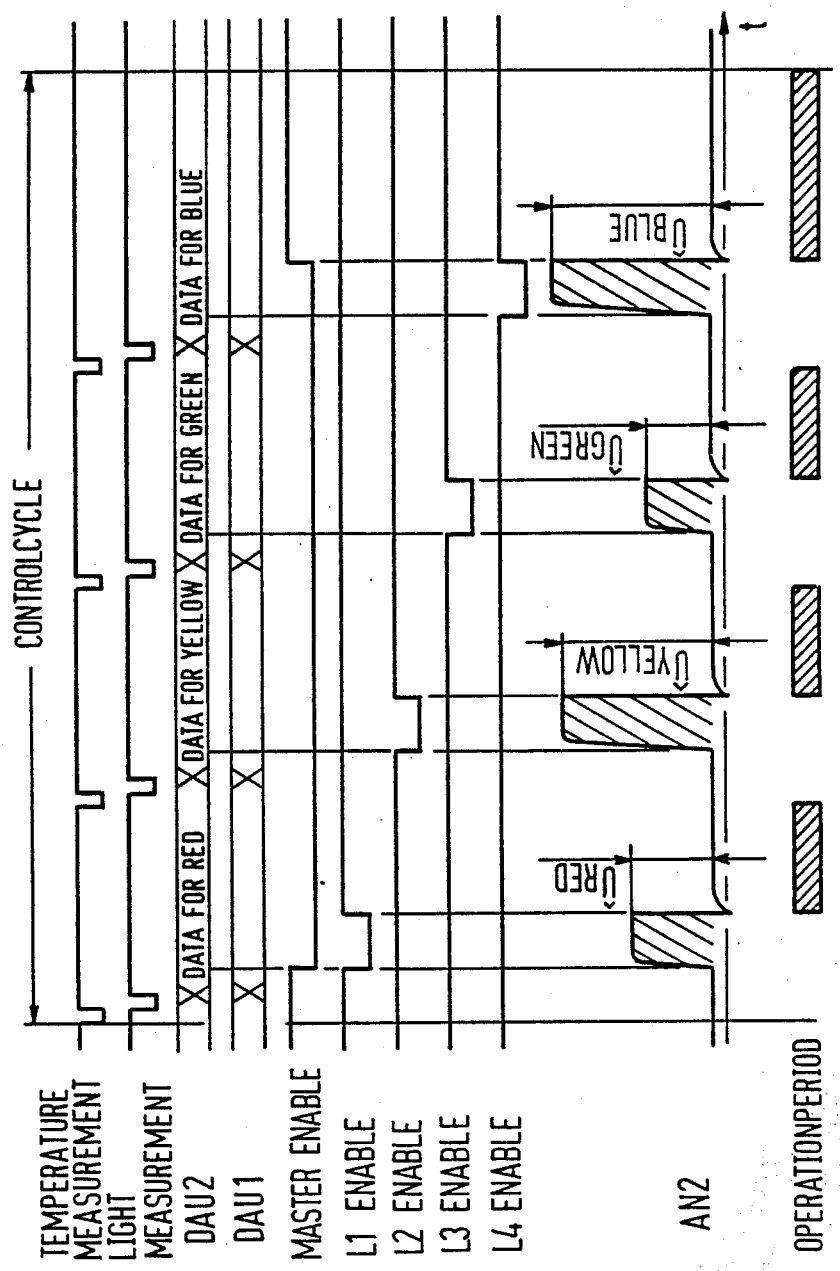

COLOR SENSOR SYSTEM FOR THE RECOGNITION OF OBJECTS WITH COLORED SURFACES

BACKGROUND OF THE INVENTION

1. Field of the Invention

The invention relates to a color sensor system for the recognition of objects with surfaces that are at least partially colored.

2. Description of the Prior Art

In conventional color recognition devices operating according to a three-area process, the objects to be recognized are illuminated with, for example, white light from a halogen lamp. The reflected light is decomposed by means of lenses and standard color filters into the primary colors, red, green and blue. The intensity of the individual color components is then converted into electrical signals by photosensors which are connected to receiving amplifiers. The amplified electrical signals are fed into an arithmetic unit for a color determination. It has also already been suggested that instead of standard color filters with following photosensors, color-sensitive photodiodes to which the light reflected from a colored object is fed through an objective lens, should be used. In this case, for a color determination, a temperature compensation is made for the electrical signals supplied by the photodiodes.

In addition, a color sensor system is already known (European Published patent application No. EP-A-0 109 686), which has a plurality of electronic light transmitters emitting light of various wavelengths, which, in succession, briefly illuminate an object whose color is to be determined with light pulses of the same intensity. The light reflected from the object is conducted to a photosensor, which converts the light signals into electrical signals and conducts the latter to an evaluation device for an evaluation. In the course of this evaluation, the presence of the color components determined by the individual light transmitters is checked with the aid of a threshold-value indicator on the basis of the electrical signals that occur in succession only. On the other hand, no provision is made for a quantitative evaluation of the intensity of the individual color components, such as is necessary, for example, for a determination of arbitrary mixed colors.

Accordingly, it is the object of the present invention to describe a color sensor system by means of which a color determination with a high degree of accuracy can be made.

SUMMARY OF THE INVENTION

In accordance with the principles of the invention, this object is achieved by providing a color sensor system for recognition of objects having at least a partially colored surface, comprising at least three electronic light transmitters emitting light pulses in a predetermined narrow-band range of wavelengths; a transmitter control device coupled to said electronic light transmitters for establishing at least one control cycle during which said light pulses successively illuminate said colored surface of an object under examination for a brief period of time; an electronic light receiver for receiving light reflected from said colored surface in response to the arrival of each of said light pulses and converting them into individual electrical signals having an intensity corresponding to that of said reflected light; an evaluation device coupled to said electronic light receiver for making a color recognition determination based on the intensity of said received individual electrical signals in the course of said control cycle; at least one temperature sensor for supplying temperature data with regard to an ambient temperature to said transmitting control device and said evaluation device, wherein said transmitting control device supplies in the course of said control cycle to said electronic light transmitters current pulses which are individually determined in accordance with said temperature data and stored data relating to temperature-dependent emission curves of said light transmitters for successively illuminating said colored surface with light pulses of predetermined intensity, and wherein said evaluation device makes a compensation for said received individual signals based upon said temperature data and stored data relating to temperature-dependent conversion curves of said light receiver; and means for comparing said received individual electrical signals with stored values for said color recognition determination.

The invention has the advantage that a color measurement of high precision can be made with the color sensor system even under varying environmental conditions, such as fluctuations in the ambient temperature and/or variations in the incidence of ambient light on the object to be measured.

Another advantage consists of the fact that the color sensor system is fully electronic in design. Through the elimination of the mechanical-optical devices that were to some extent necessary according to the state of the art, the color sensor system in accordance with the invention can be manufactured considerably more advantageously, not only in terms of cost, but also in terms of volume and weight. Volume and weight are of particular importance when such a color sensor system is to be introduced in control devices or, for example, automatic manipulating systems (robots).

An advantageous embodiment of the invention is designed so that each of the light transmitters consists of a light emitting diode in a Predetermined narrow-band wavelength range and a transmitting optical waveguide connected with it, so that the light receive consists of a photo semiconductor and a receiving optical waveguide connected with it, and so that the free ends of the transmitting optical waveguide are arranged concentrically in a sensor head around the free end of the receiving optical waveguide. This has the advantage that, on the one hand, the light transmitter and the light received can be constructed with only a small amount of circuitry and, on the other, that as a result of the optical waveguides that are assembled together in one sensor head, the color sensor system can be used flexibly for any desired application.

Another advantageous embodiment is designed so that the transmission control device and the evaluation device are formed jointly from a micro-controller system.

The advantages of these embodiments are that the color sensor system is provided with devices that can be manufactured with only a small amount of circuitry, to control the light transmitters or to evaluate the electrical signals supplied by the light receiver.

Other features and advantages of the invention will be apparent from the description of the preferred embodiments, and from the claims.

For a fuller understanding of the present invention, reference should now be made to the following detailed description of a preferred embodiment of the invention and to the accompanying drawings.

BRIEF DESCRIPTION OF THE DRAWINGS

FIG. 6 illustrates a schematic time diagram.

DETAILED DESCRIPTION OF THE PREFERRED EMBODIMENT

Figure 1:
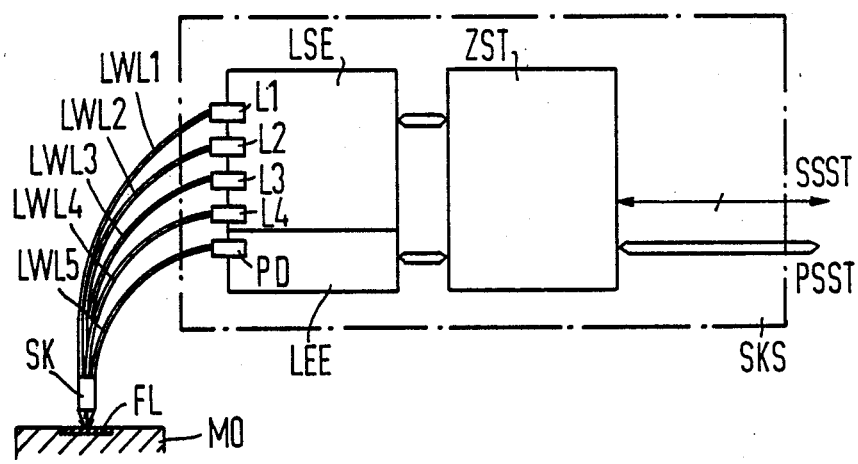
FIG. 1 illustrates a block circuit diagram of a color sensor system according to the present invention.

FIG. 1 illustrates a block circuit diagram of a color sensor system. It consists of a sensor head SK, which is arranged at a determined distance from an object that is to be identified (measurement object) MO. A part of the surface of the object MO has been marked with a color. In the sensor head SK are arranged four transmitting optical waveguides LWL1 to LWL4 and a receiving optical waveguide LWL5 with its free ends. The transmitting optical waveguides LWL1 to LWL4 are each connected by their other end with an electronic light transmitter. The light transmitters, which are designated L1 to L4 in accordance with their assignment to the transmitting optical waveguides LWL1 to LWL4, form the outputs of a sensor-head-control device SKS. In the embodiment presented here, light emitting diodes (LEDs) are used as light transmitters, each of which emits light in a predetermined narrow-band range of wavelengths. The dominant wavelengths selected are 660 nm (red), 585 nm (yellow), 555 nm (green), and 480 nm (blue) with the tolerance in each case amounting to ±15 nm. These LEDs are connected to a light-transmitting device LSE, which can be controlled from a central control system ZST through a circuit arrangement.

The receiving optical waveguide LWL5 is connected to a photo semiconductor PD, which might, for example, be a photodiode. This photo semiconductor, which forms an input of the sensor-head-control device SKS mentioned above, is connected to a light-receiving device LEE, which is connected in turn, through a circuit arrangement, with the central control system ZST, also mentioned above. This central control system ZST may also have, for example, a serial interface SSST and a parallel interface PSST, by means of which it may be connected to external devices such is automatic manipulation systems.

For the recognition of an object with a colored surface, the central control device ZST feeds control signals in a control cycle to the light-transmitting device LSE. In response to these control signals, the LEDs L1 to L4 are subjected in succession to current pulses which might have a duration of from 200 to 500 µs, resulting in a corresponding emission of light pulses. The colored surface of the object MO to be identified is illuminated briefly with these light pulses through the sensor head SK. The light that is reflected in each case from the colored surface upon the occurrence of the individual light pulses is received, through the sensor head SK and the receiving optical waveguide LWL5, by the photo semiconductor PD and converted into an electrical signal. The electrical signals that are emitted successively by the photo semiconductor in the course of a control cycle are then conducted through the light-receiving device LEE to the central control system ZST for a color determination. The color determination can be accomplished according to known arithmetical methods, as are given, for example, in the German Industrial Standards (DIN) formula compilations DIN 5053, 6174, 6175 and 55951, or according to a "TEACH-IN" principle described below, depending on whether or not the spectral emission curves of the LEDs correspond to the standard colormetric spectra.

In this connection it should be noted that, while it is true that according to the process used three light transmitters each emitting light in a predetermined range of wavelengths (red, green, blue) are sufficient for a color determination, however, in order to increase the number of colors that can be distinguished, the number of light transmitters in the embodiment described here will be raised to four. If necessary, this number can be increased further.

Figure 2:
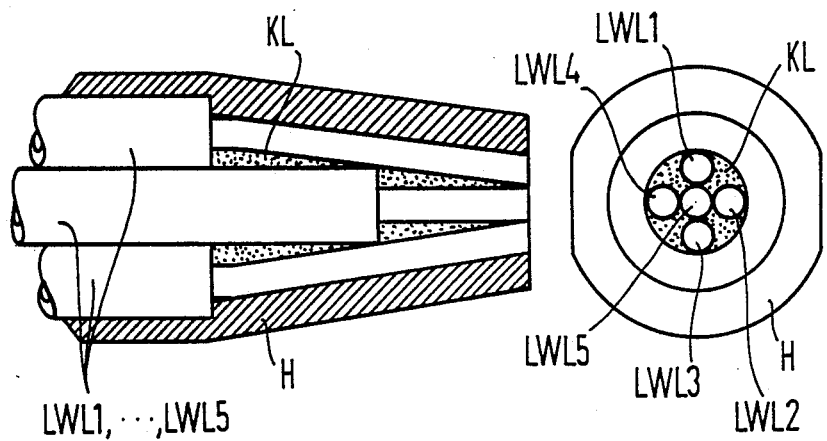
FIG. 2 illustrates a cross-sectional view of the sensor head, which is shown only schematically in FIG. 1.

FIG. 2 shows an axial cross section and a front view of the sensor head. According to this drawing, the free ends of the transmitting optical waveguides LWL1 to LWL4 and of the receiving optical waveguide LWL5 are placed in a sensor sheath H, which tapers conically in the direction of the measurement object, and fixed there in position with the aid of a suitable adhesive KL. The receiving optical waveguide LWL5 is mounted in the center of the sensor sheath H and is surrounded concentrically by the transmitting optical waveguides LWL1 to LWL4. The stripped ends of the optical waveguides that are arranged in the sensor head are, in addition, provided with an opaque coating, which might be applied by spraying on a color, in order to prevent crosstalk between the individual waveguides.

Otherwise, FIG. 2 illustrates only a possible embodiment for a sensor head. A sensor head of this kind can, however, also be made according to a different design, depending on the application of the color sensor system.

Figure 3:
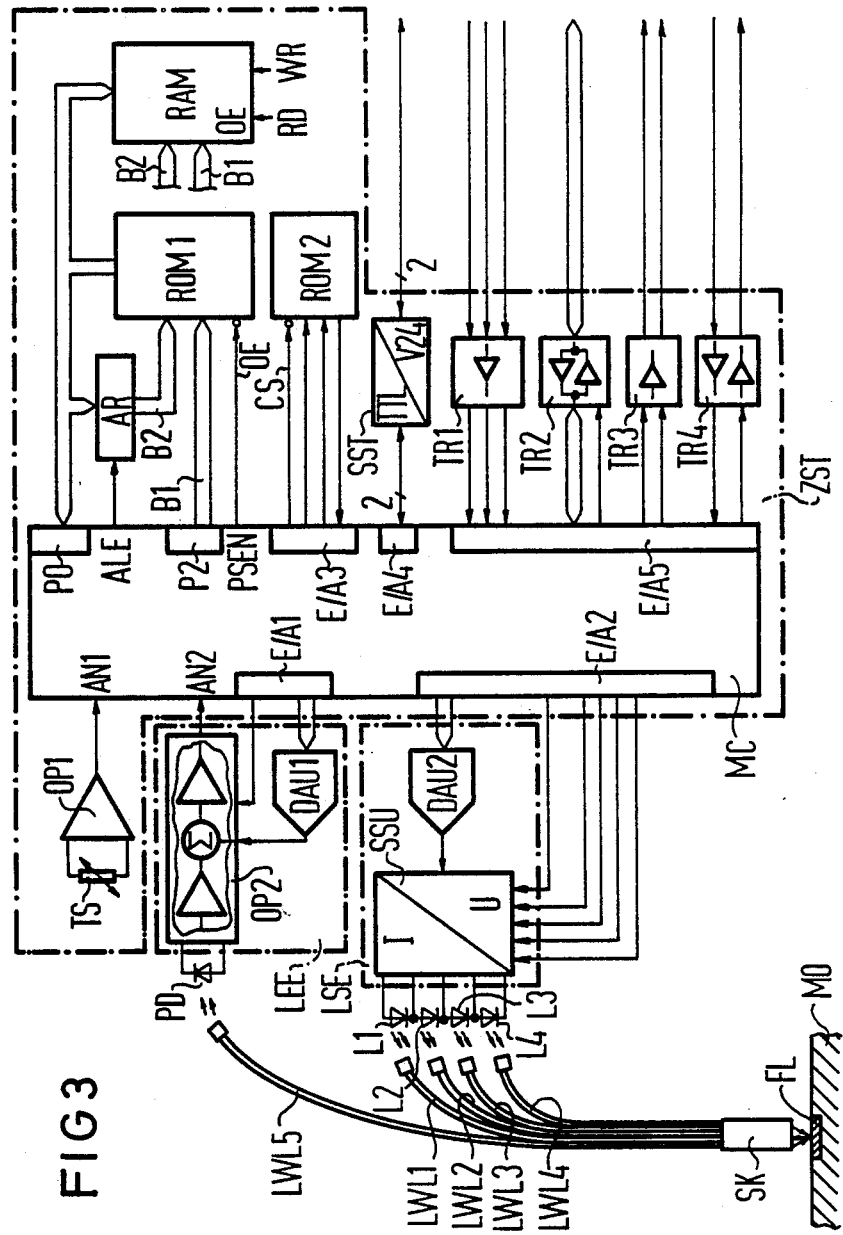
FIG. 3 illustrates a detailed block circuit diagram of the color sensor system shown in FIG. 1.

In FIG. 3, the color sensor system described above is illustrated in greater detail. The central control system ZST that appears in FIG. 1, which, as mentioned above, serves both as a transmission control device and an evaluation device, consists, in this embodiment, of a micro-controller. In this case, it might, for example be one of the micro-controllers supplied by Siemens AG under the designation SAB 80535. In FIG. 3, only those terminals of this micro-controller that are necessary for an understanding of the mode of operation of the color sensor system are shown schematically. Accordingly, there are shown two analog channels AN1 and AN2, digital in-and-output terminal groups E/A1 to E/A5, in-and-output channels P0 and P2, and control terminals ALE and PSEN. The terminals that are combined in the in-and-output terminal groups are terminals that, in the abovementioned SAB 80535 micro-controller, are assigned to the total of six available in-and-output channels (Port 0 to Port 5).

The control programs that are required for the operation of the color sensor system are stored in an external read-only memory ROM1. For this purpose, erasable read-only memories (EPROM) might be used. In the present embodiment, the read-only memory is mounted in a socket, so that, depending on the application of the color sensor system, read-only memories with varying storage capacities may, if necessary, be used for the control programs. The read-only memory ROM1 is controlled by the micro-controler MC in a known manner through the in-and-output channels P0 and P2, and the control lines ALE and and PSEN. By means of a control signal transmitted over the control line PSEN, the read-only memory ROM1 is enabled for an access. On the other hand, the temporary storage of the address signal used to address the storage cells in the read-only memory ROM1 in an address register AR is controlled over the control line ALE. Another read-only memory ROM2 is connected with the micro-controller MC through the in-and-output terminal group E/A3. In this read-only memory are stored the calibration and control data that are required for the operation of the color sensor system, which will be discussed in greater detail below. The read-only memory in this case might consist, for example, of at least one electrically erasable read-only memory ($E^2PROM$) that can be activated serially. Electrically erasable read-only memories that can, for example, also be activated in parallel can, however, also be used; they can be activated through the abovementioned in-and-output channels P0 to P2.

The light-transmitting device LSE that is connected to the LEDs L1 to L4 and has been described above is also connected to the in-and-output terminal group E/A2. This device consists of a digital/analog converter DAU2 and a voltage-current converter SSU with an impressed output current, with which the LEDs L1 to L4 are activated. This voltage-current converter has five control inputs which are connected through the in-and-output terminal group E/A2 with the micro-controller MC. At the beginning of a control cycle for the driving of the LEDs, the voltage-current converter SSU is first activated through one of the control inputs (MASTER ENABLE in FIG. 6). Then the LEDs are subjected one after the other to a Predetermined current pulse. A voltage corresponding to these current pulses is received by the voltage-current converter SSU, conducted through the digital/analog converter DAU2 (DAU2, L1 ENABLE, ..., L4 ENABLE in FIG. 6). The current pulses for the individual LEDs are determined in the course of a calibration procedure in such a manner that the light pulses emitted from the LEDs in each case, upon reflection at a white standard pattern, produce electrical signals of the same intensity at the output of the photo semiconductor PD.

Connected to the analog channel AN1 is a temperature sensor, which consists, for example, of a negative temperature coefficient (NTC) resistor TS and an operational amplifier OP1 connected with it, and which supplies a measurement value for the ambient temperature. In accordance with the temperature data that are thus supplied and data with regard to the temperature-dependent emission curve of the LEDs L1 to L4, which are stored in the above-mentioned read-only memory ROM2, the micro-controller MC feeds a digitally coded voltage value corresponding to the nominal current for the LEDs to the digital analog converter DAU2. Connected to the analog channel AN2 is the output of the light-receiving device LEE described above. This device consists of a multi level operational amplifier unit OP2, of which there is shown a series circuit consisting of two operational amplifiers and a summing element inserted between them. The summing element is also connected to the output of a digital/analog converter DAU1, which is connected to the in-and-output terminal group E/A1. Through it, the operational amplifier unit OP2 receives from the micro-controller compensation signals for a compensation of offset voltage caused by failing voltage and/or interfering light components.

Failing voltages can, for example, be caused by a spread in the conversion curve of the photo semiconductor that is used and/or in the amplification of the operational amplifier unit, as well as through a temperature dependence of the conversion curve of the photo semiconductor. The component of the compensation signal resulting from the temperature dependence of the conversion curve is, in this case, formed by the micro-controller MC in accordance with the temperature data supplied by the temperature sensor described above (TEMPERATURE-MEASUREMENT in FIG. 6) and data with regard to the temperature-dependent conversion curve of the photo semiconductor, which are stored in the read-only memory unit ROM2 that has been described earlier.

Interfering light components, on the other hand, may be caused by ambient light that is received by the photo semiconductor. In order to compensate for components of this kind, in the present embodiment, at the beginning of each control cycle before any activation of the LEDs L1 to L4, a light measurement is made (LIGHT MEASUREMENT in FIG. 6) and compensation signal component corresponding to the ambient light received is formed. From this compensation signal component and the compensation signal component that takes the failing voltages into account, there is then formed a total compensation signal, which is conducted to the operational amplifier unit OP2 for the duration of a control cycle (DAU1 in FIG. 6).

The micro-controller MC can make an absolute or a relative color determination, as desired, through arithmetical and logic operations (OPERATION-PERIOD in FIG. 6), on the basis of the electrical signals (AN2 in FIG. 6) conducted to its successively in the course of a control cycle through the analog channel AN2. For this purpose there are stored in the read-only memory unit ROM2, on the one hand, color limit values in a digitally coded form, within which the micro-controller makes an absolute color determination, that is, it computes a value lying within these color limit values and supplies a corresponding digitally coded signal. On the other hand, it is also possible to store fixed color values that are to be computed in the read-only memory unit ROM2 in a digitally coded form. For example, 16 different color values with tolerance data can be prescribed, which are to be recognized by the micro-controller MC (TEACH-IN principle). For this purpose, in the course of a TEACH-IN procedure, colored patterns that correspond to the color values that are to be recognized are successively illuminated for a brief time in the course of a control cycle by the light pulses emitted by the LEDs Li, ..., L4. The electrical signals that occur as a result one after another at the output of the photo semiconductor PD for the individual color values and which correspond to the individual color components of the respective color value, are digitally coded and stored according to the color value in the read-only memory unit ROM2, that is, in the present embodiment, four digitally coded color components are stored for each color value, corresponding to the four LEDs.

During the operation of the color sensor system, the micro-controller then compares, for a color determination of an object, in the course of a control cycle, the four electrical signals fed to it in succession after they have been digitalized with the color components of the color values stored in the read-only memory unit ROM2 and emits a corresponding digital indicator signal. This signal tells whether the color of the illuminated object corresponds to a stored color value. In this case, for a known color value, there can be given, for example, either a color code corresponding to this value or the color components belonging to it. When an unfamiliar color is computed, on the other hand, in the present embodiment, data can also be included in the report signal with regard to the stored color value that comes closest to the unfamiliar color, in the form of a color code or the color components.

Additionally, the color determination proceeds in the following manner: In the course of a control cycle, upon each occurrence of a signal corresponding to a specific color component at the input AN2 of the micro-controller MC, a comparison (designated in FIG. 6 by OPERATION-PERIOD) is made immediately with the color components of the stored color values that are relevant in each case. In the course of the first three comparison procedures, in each case those stored color values are determined which are to be included in the subsequent comparison procedure. Thus, by means of the first three comparison procedures, the possible color values have already been selected to such an extent that upon the last comparison procedure in the control cycle, the result of the color determination is immediately available and, as a result, the emission of a indicator signal can take place.

In the event that the emission curves of the LEDs correspond to the standard colormetric spectra, the color determination can also be made, as mentioned above, according to known arithmetical processes. To carry out the arithmetical operations, the micro-controller MC can, for example, be assisted by an arithmetic processor.

The in-and-output terminal groups E/A 4 and E/A5 shown in FIG. 3 represent the interfaces designated by SST and PSST in FIG. 1. The in-and-output terminal group E/A4 in this case can form, for example, together with an interface unit SST, a standardized serial RS232C/V24 interface. In the case of the parallel interface that is formed by the in-and-output terminal group E/A5, a so-called Centronix interface might, for example, be formed. Driver stages TR1 to TR3 are inserted in the individual interface lines of this interface.

Through the interfaces that have just been described, the color sensor system explained above can communicate with external devices, in order, for example, to receive control signals commanding a color determination from an external device or, after a color determination, to give the indicator signals relating to the recognized color to the external device in question. In addition, through this interface the prescribed color limit values or color values for an absolute or relative color determination, as described above, can be fed into the system.

In addition to the interfaces mentioned above, an interface consisting of an interrupt-input and interrupt-output has also been provided. Driver stages TR4 (FIG. 3) have been inserted in the interface lines. Over these interface lines, interrupt signals can be given or received by the micro-controller MC at all times, if in specific emergency situations, such as misfunctionings of the color sensor system or the external device connected to it, a signal transmission over the above-mentioned interfaces is insufficient from the point of view of speed.

In addition, it should be noted that the color values computed by the micro-controller MC within a prescribed time interval can be stored in a write-read memory unit designated by RAM in FIG. 3, so that, for example, they can subsequently be statistically evaluated.

Figure 4:
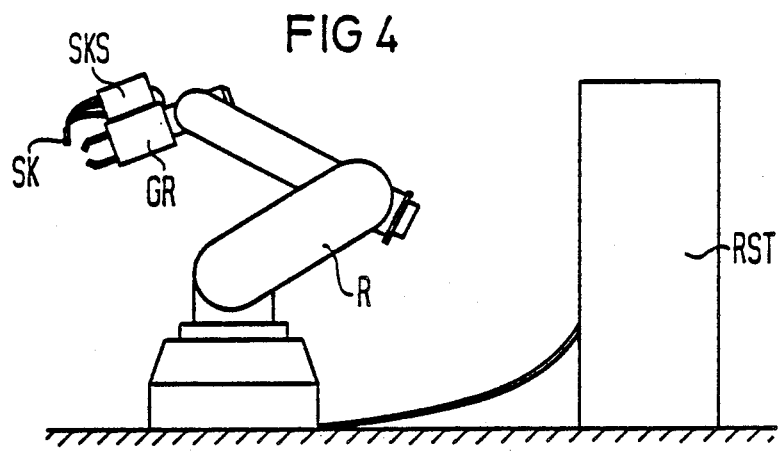
FIGS. 4 and 5 illustrate two possible applications for color sensor systems.
Figure 5:
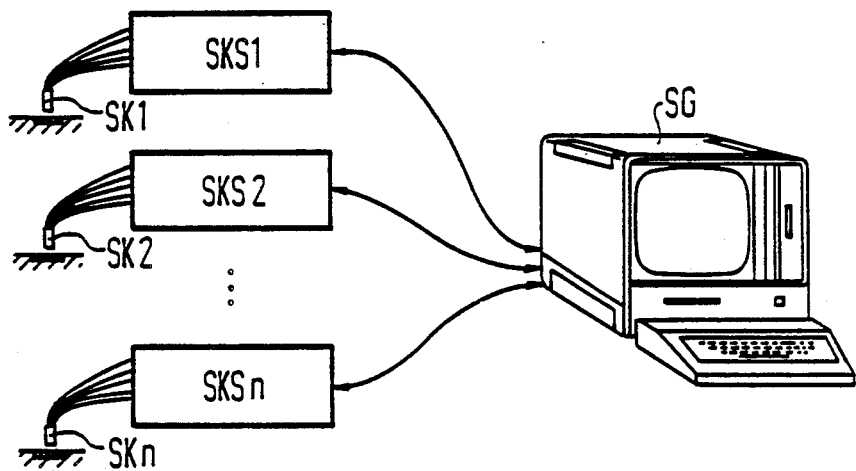

The color sensor system explained above with the aid of FIGS. 1 to 3 can be used generally for measurement and control purposes. Two possible applications are shown in FIGS. 4 and 5. The arrangement illustrated in FIG. 4 involves a robot R which is controlled by a robot control RST. In the gripper GR of this robot has been introduced a color sensor system of the kind described above for the recognition of colored objects. The gripper GR is controlled according to the measurement results supplied by this color sensor system. In this case the measurement results supplied by the color sensor system can be conducted, depending on the design of the robot, either directly to the gripper or to the robot control RST, over one of the two interfaces of the color sensor system that have been described above.

The arrangement illustrated in FIG. 5 involves a control device to which a large number of color sensor systems (SK1, SKS1; . . . ; SKn, SKSn) have been connected, in each case through a serial interface with a central control device, for example, in the form of a personal computer. Such an arrangement can be used, for example, in manufacturing processes for monitoring a conveyor belt on the basis color-marked objects.

Thus, there has been shown and described novel color sensor system which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. All such changes, modifications, variations and other uses and applications which do not depart from the spirit and scope of the invention are deemed to be covered by the invention which is limited only by the claims which follow.

I claim:

1. A color sensor system for the recognition of objects having at least a partially colored surface, comprising:
   at least three electronic light transmitters, each emitting light pulses in a predetermined narrow-band range of wavelengths;
   a transmitter control device coupled to said electronic light transmitters for establishing at least one control cycle during which said light pulses successively illuminate said colored surface of an object;
   an electronic light receiver for receiving light reflected from said colored surface in response to the arrival of each of said light pulses and converting them into individual electrical signals having an intensity corresponding to that of said reflected light;
   an evaluation device coupled to said electronic light receiver for making a color recognition determination based on the intensity of said received individual electrical signals in the course of said control cycle;
   at least one temperature sensor for supplying temperature data with regard to an ambient temperature to said transmitting control device and said evaluation device, wherein said transmitting control device supplies in the course of said control cycle to said electronic light transmitters current pulses which are individually determined in accordance with said temperature data and stored data relating to temperature-dependent emission curves of said light transmitters for successively illuminating said colored surface with light pulses of predetermined intensity, and wherein said evaluation device makes a compensation for said received individual signals based upon said temperature data and stored data relating to temperature-dependent conversion curves of said light receiver; and means for comparing said received individual electrical signals with stored values for said color recognition determination.

2. The color sensor system according to claim 1, further comprising means for measuring the ambient light, said means for measuring supplying ambient light data to said evaluation device in the course of each said control cycle for compensating each individual signal.

3. The color sensor system according to claim 1, wherein said evaluation device includes storage means for storing color limit values as comparative color values for making an absolute color measurement, and storing predetermined color values for making a relative color measurement.

4. The color sensor system according to claim 1, wherein each of said light transmitters comprises a light emitting device for emitting said light of a predetermined narrow-band range of wavelengths, and a transmitting optical waveguide coupled thereto; and said light receiver comprises a photo semiconductor and a receiving optical waveguide coupled thereto, the free ends of said transmitting optical waveguides being arranged concentrically in a sensor head around the free end of said receiving optical waveguide.

5. The color sensor system according to claim 2, wherein each of said light transmitters comprises a light emitting device for emitting said light of a predetermined narrow-band range of wavelengths, and a transmitting optical waveguide coupled thereto; and said light receiver comprises a photo semiconductor and a receiving optical waveguide coupled thereto, the free ends of said transmitting optical waveguides being arranged concentrically in a sensor head around the free end of said receiving optical waveguide.

6. The color sensor system according to claim 3, wherein each of said light transmitters comprises a light emitting device for emitting said light of a predetermined narrow-band range of wavelengths, and a transmitting optical waveguide coupled thereto; and said light receiver comprises a photo semiconductor and a receiving optical waveguide coupled thereto, the free ends of said transmitting optical waveguides being arranged concentrically in a sensor head around the free end of said receiving optical waveguide.

7. The color sensor system according to claim 1, wherein said light transmitters each include at least one light emitting device, said light emitting devices being jointly coupled to a current control device, which receives from said transmission control device control signals corresponding to said current pulses that are supplied individually to said light transmitters, and wherein the output of said light receiver is coupled to the input of a regulating amplifier, which receives, conducted from said evaluation device, compensation signals for the compensation of said individual electrical signals.

8. The color sensor system according to claim 2, wherein the supplying of the temperature data and the measurement of the ambient light occurs within a control cycle before the emission of at least the first of said current pulses by said transmission control device.

9. A color sensor system for the recognition of objects having at least a partially colored surface, comprising:

at least three electronic light transmitters each emitting light pulses in a predetermined narrow-band range of wavelengths;

an electronic light receiver for receiving light reflected from said colored surface in response to the arrival of each of said light pulses and converting them into individual electrical signals having an intensity corresponding to that of said reflected light;

a micro-controller system coupled to said electronic light transmitters for establishing at least one control cycle during which said light pulses successively illuminate said colored surface of an object and coupled to said electronic light receiver for making a color recognition determination based on the intensity of said received individual electrical signals in the course of said control cycle;

at least one temperature sensor for supplying temperature data with regard to an ambient temperature to said micro-controller system which supplies in the course of said control cycle to said electronic light transmitters current pulses which are individually determined in accordance with said temperature data and stored data relating to temperature-dependent emission curves of said light transmitters for successively illuminating said colored surface with light pulses of predetermined intensity, and wherein said micro-controller system makes a compensation for said received individual signals based upon said temperature data and stored data relating to temperature-dependent conversion curves of said light receiver and, compares said received individual electrical signals with stored values for said color recognition determination.

10. The color sensor system according to claim 9, wherein said micro-controller system is coupled to external devices through at least one serial and at least one parallel interface and through interrupt inputs and outputs.

11. The color sensor system according to claim 9, wherein said micro-controller system includes storage means for storing color limit values as comparative color values for making an absolute color measurement, and storing predetermined color values for making a relative color measurement.

12. The color sensor system according to claim 9, wherein each of said light transmitters comprises a light emitting device for emitting said light of a predetermined narrow-band range of wavelengths and a transmitting optical waveguide coupled thereto; and said light receiver comprises a photo semiconductor and a receiving optical waveguide coupled thereto, the free ends of said transmitting optical waveguides being arranged concentrically in a sensor head around the free end of said receiving optical waveguide.

13. The color sensor system according to claim 9, wherein said light transmitters each include at least one light emitting device; said light emitting devices being jointly coupled to a current control device, which receives from said micro-controller system control signals corresponding to said current pulses that are supplied individually to said light transmitters, and wherein the output of said light receiver is coupled to the input of a regulating amplifier, which receives, conducted from said micro-controller system, compensation signals for the compensation of said individual electrical signals.

* * * * *